United States Patent
Chiang et al.

(10) Patent No.: US 6,285,905 B1
(45) Date of Patent: Sep. 4, 2001

(54) TWO-WAY MEDICAL TREATMENT APPARATUS

(75) Inventors: Chih-Cheng Chiang, 13F-1, No. 147-8, Mei-Chuan W Rd., Taichung City; Ho-Yen Tseng, Taichung, both of (TW)

(73) Assignee: Chih-Cheng Chiang, Taichung (TW)

( * ) Notice: Subject to any disclaimer, the term of this patent is extended or adjusted under 35 U.S.C. 154(b) by 0 days.

(21) Appl. No.: 09/339,169

(22) Filed: Jun. 24, 1999

(51) Int. Cl.[7] .................................................. A61N 1/35
(52) U.S. Cl. ........................ 607/2; 607/76; 600/554; 600/548; 128/907
(58) Field of Search ............................ 607/3.2, 45–48, 607/50, 58, 65, 76; 128/907; 600/9–11, 13–15, 548, 554

(56) References Cited

U.S. PATENT DOCUMENTS

| | | | |
|---|---|---|---|
| 4,966,164 | * 10/1990 | Colsen et al. | 128/907 |
| 5,366,483 | * 11/1994 | Sadhkin | 607/3 |
| 5,546,954 | * 8/1996 | Yamada | 128/735 |
| 5,957,862 | * 9/1999 | Lu et al. | 600/548 |

* cited by examiner

Primary Examiner—Jeffrey R. Jastrzab
(74) Attorney, Agent, or Firm—Bacon & Thomas, PLLC

(57) ABSTRACT

A two-way medical treatment apparatus includes a housing containing an electronic, oscillation generator capable of generating an oscillating current, and an electrode unit capable of being plugged into the housing to receive the oscillating current. The electrode unit includes a probe and a conducting body. The conducting body is shaped to fit within the ear of a patient, and the probe is arranged to touch inductive reflecting zones in the palm or foot of the patient, as well as any possible curing points other than the vital points, to form a closed circuit. The probe includes magnetic elements that transform the oscillating current into an electromagnetic wave in order to simultaneously stimulate the ear, palm, or bottom of the foot and thereby simulate the effect of acupuncture needles in order to diagnose diseased organs, and further to perform treatment.

6 Claims, 7 Drawing Sheets

TWO-WAY MEDICAL TREATMENT APPARATUS

BACKGROUND OF THE INVENTION

The present invention relates to a two-way medical treatment apparatus, and more particularly to a two-way medical treatment apparatus that makes use of oscillating electric current to stimulate the vital points at the hands and ears in order to diagnose the cause of a disease and further to achieve the function of medical treatment.

According to the theory of Chinese medical treatment, it has been quite popular to cure various kinds of diseases by means of acupuncture, which stimulates the vital points of various portions of the human body. However, needles used in acupuncture treatment of multiple patients may transmit infection. Also, because of the individual constitution of the body of certain patients, rejection of the needles may occur and the acupuncture may cause needle sickness of the patient. Therefore, various kinds of medical treatment apparatus have been proposed which make use of oscillating electric current to stimulate various vital points of human body in order to achieve the function of medical treatment. However, the conventional electrical medical treatment apparatus are all relatively big and expensive, and therefore are used only in hospitals and are not able to achieve the function of self-health-care. Although some of those apparatuses are portable, most of them possess only a single function for stimulating the vital points at the palms or ears similar to the treatment by acupuncture and are for treatment after the illness has occurred rather than for prevention. Therefore, they are not suitable for the function of self-health-care.

In view of the foregoing disadvantages, the present invention is provided for diagnosing the cause of diseases and for curing the diseases. The present invention makes use of the theory of Chinese medical treatment that wherever there is a disease in any organ of our body, a corresponding vital point at the ears or on the palms will generate a positive reaction resulting from a change in magnetic field of the micro-circulation due to the change in impedance generated by the feeling of pain, thereby generating electric current.

SUMMARY OF THE INVENTION

The primary objective of the present invention is to provide a two-way medical treatment apparatus which can provide a two-way treatment function at the vital points on the palm or at the foot or at the ear simultaneously in a manner similar to treatment by acupuncture.

The secondary objective of the present invention is to provide a two-way medical treatment apparatus which can provide electric current to generate an electric field in order to diagnose the diseased organ and further to provide treatment.

The embodiment of the present invention in order to achieve the foregoing objective is described as follows:

The present invention is a two-way medical treatment apparatus which comprises:

an electronic oscillation generator capable of generating oscillating current, a housing, and an electrode unit which is able to plug into the housing, An end of the electrode unit includes a probe including a magnetic element and an electrode as well as an additional conducting body. The conducting body of the electrode unit is plugged into the ear while the probe electrode touches the inductive reflecting zone of the palm or foot and any possible curing points other than the vital points to form a closed circuit. The present invention then makes use of the electronic oscillation generator and the magnetic element to transform a current into an electromagnetic wave in order to simultaneously stimulate the ear, the palm, or the foot to provide a function similar to that of an acupuncture needle in order to diagnose the diseased organs, and further to perform treatment. In this way, a two-way enhanced curing effect is achieved.

For a better understanding of the present invention, reference will now be made by way of embodiments to the accompanying drawings:

DETAIL DESCRIPTION OF THE INVENTION

Figure 5:
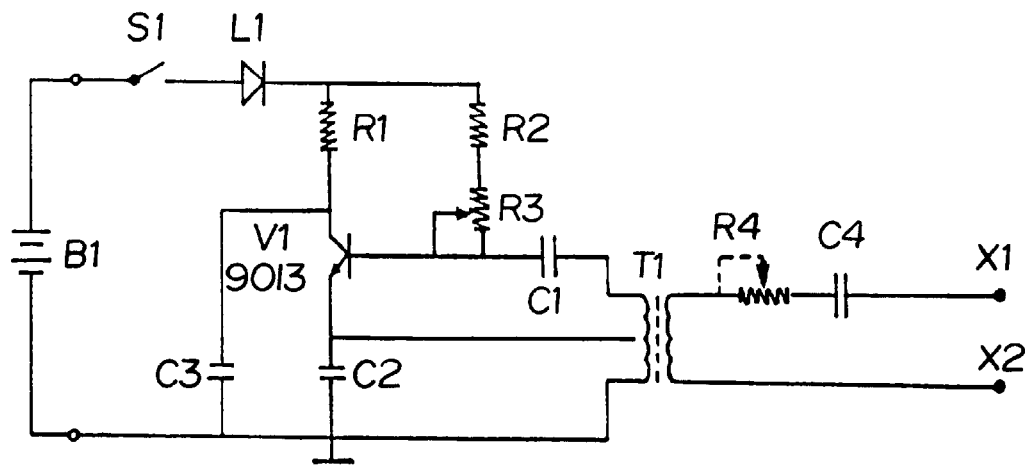
FIG. 5 is a circuit diagram of the present invention.
Figure 4:
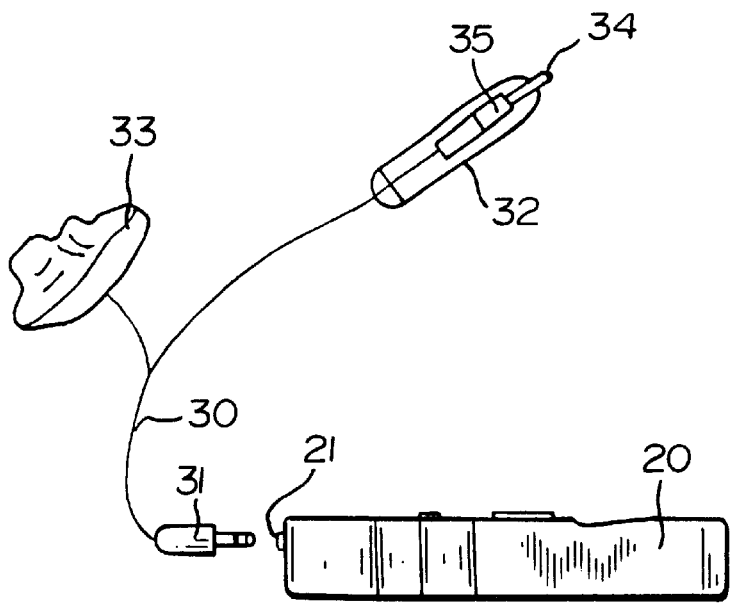
FIG. 4 is a schematic structural diagram of the present invention.
Figure 6:
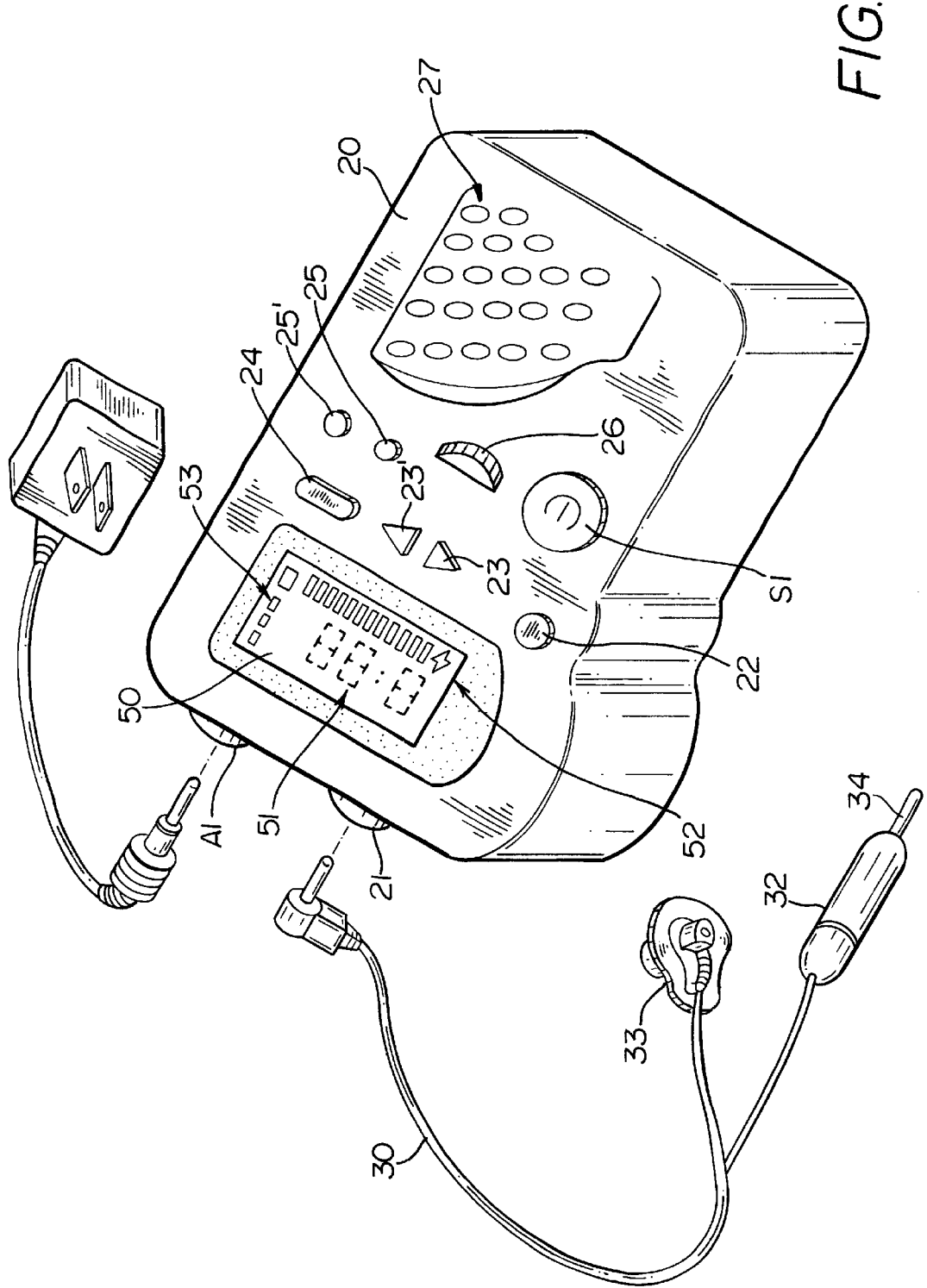
FIG. 6 is an isometric view of the present invention.
Figure 7:
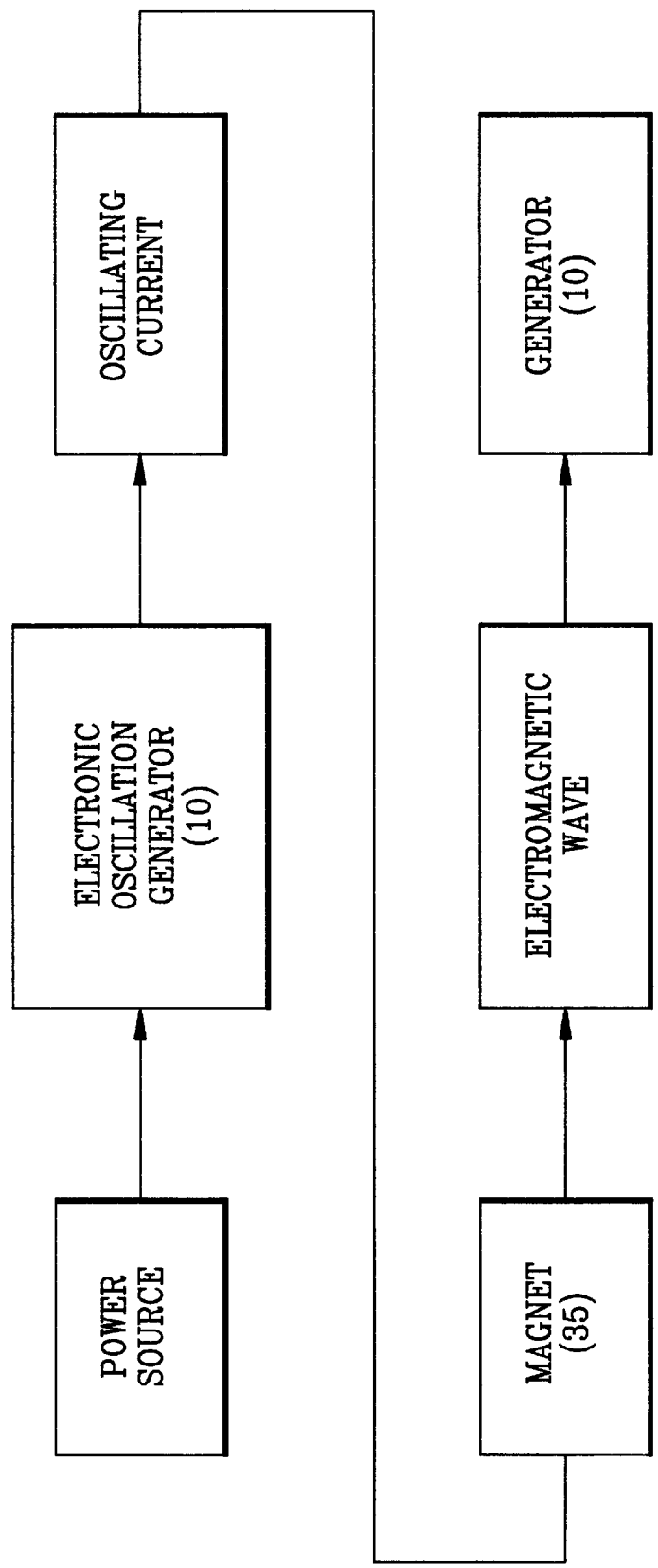
FIG. 7 is a flowchart showing generation of the electromagnetic wave of the present invention.

With reference to FIGS. 4, 5, and 6, the present invention comprises an electronic oscillation generator 10 and a housing 20. Oscillation generator 10 makes use of a battery B1 to provide a power source, or a transformer to change alternating current into direct current and provide power through a socket A1, and includes a power source switch S1 and a Light Emitting Diode (LED) L1 arranged to show if the internal operation of the treatment apparatus is normal as well a plurality of resistors R1, R2, variable resistors R3, R4, capacitors C1, C2, C3, C4, a transistor V1, and a transformer T1, to convert the DC voltage into an oscillating current output from the output terminals X1, X2.

Housing 20 contains the electronic oscillation generator 10. A plug-in hole 21 and socket A1 are set up at the top end of the housing 20, and the plug-in hole 21 is connected to the output terminals X1, X2. An LED digital display board 50 having the function of timing is set up on the housing 20, the digital display board 50 including a first display area 51 for counting time, a second display area 52 for displaying the magnitude of the electromagnetic wave, and a third display area 53 for displaying a battery charge level. A plurality of push buttons are set up below the digital display board 50 as shown in FIG. 6, including the power source switch S1, a start button 22 for the counter to reset a pre-determined time (5 minutes), two opposite push buttons 23, 23' to be connected to the variable resistor R3 to change the resistance coefficient in order to change the magnitude of the oscillating current so as to modulate the magnitude of the electromagnetic wave; a memory knob 24 for starting the memory, selection knob 25, 25' capable of switching to a different input memory, and a switching knob 26 for switching to either diagnosis or treatment. Speaker holes 27 are set up beside and below the push buttons 23, 23'.

One end of electrode unit 30 includes an electrode plug 31 for plugging into the plug-in hole 21 of the electronic oscillation generator 10. The other end is divided into a probe 32 and a conducting body 33 to be connected to the output terminals X1 and X2 respectively. The front end of the probe 32 is an electrode 34 made of magnetically conductive material. Three consecutive magnetic elements 35 are set up at the end of the electrode 34. By means of the magnetic elements 36 the electric current output from the output terminal X1 is transformed into an electromagnetic wave to be transmitted to the electrode 34, and to the conducting body 33. The conducting body 33 is made of conductive gel is in the shape of ear contour.

Figure 1:
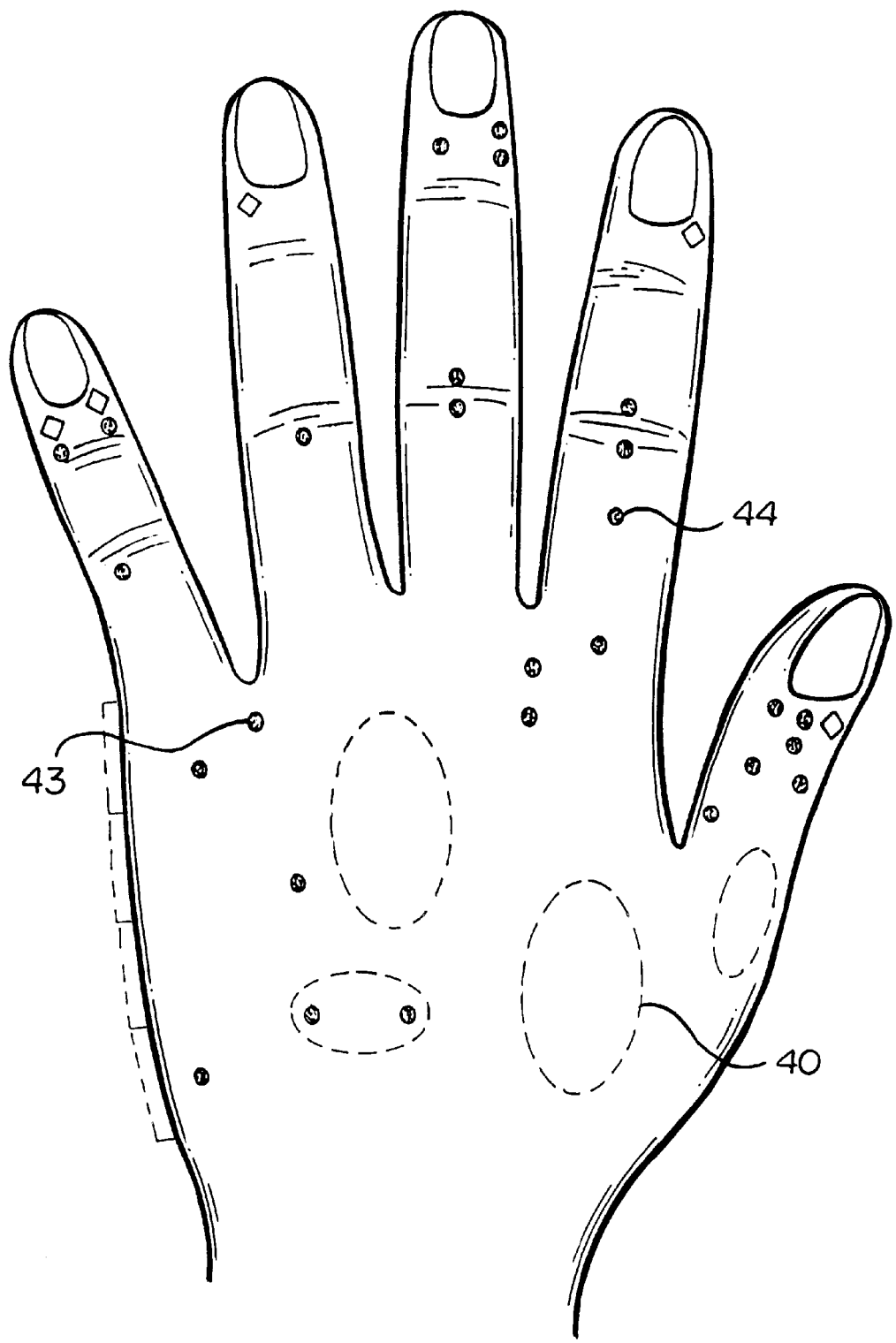
FIG. 1 is a schematic diagram of the inductive reflecting zone of the vital points on the back of the hand.
Figure 2:
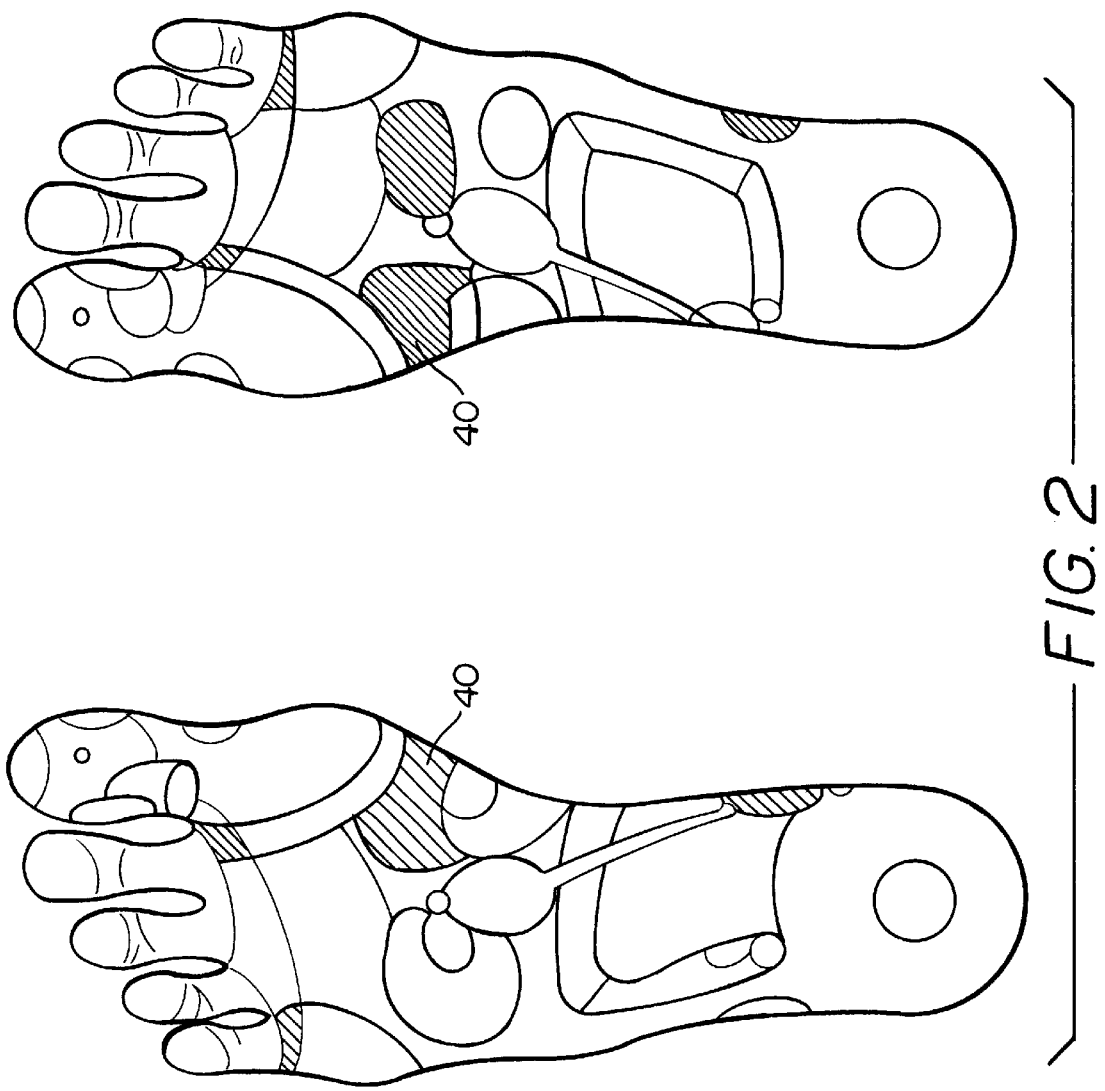
FIG. 2 is a schematic diagram of the inductive reflecting zone of the vital points on the bottom of the foot.
Figure 3:
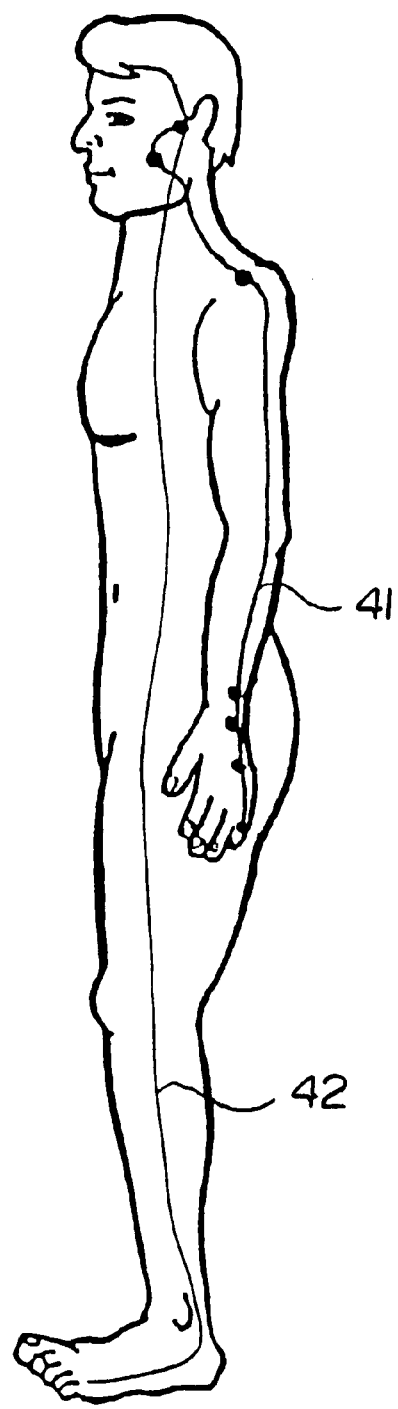
FIG. 3 is a schematic diagram of the blood vessels of human body.
Figure 8:
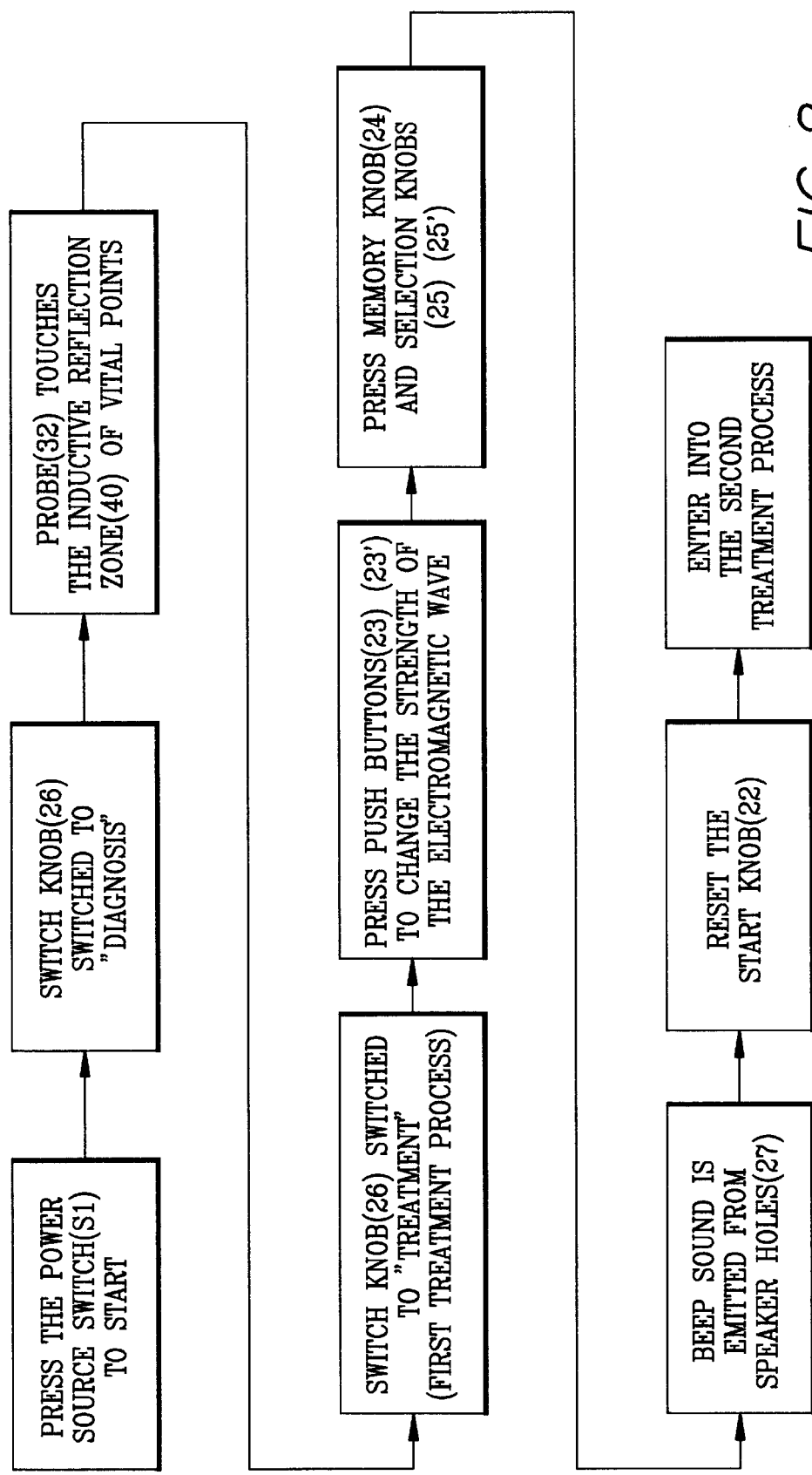
FIG. 8 is an operation flowchart of the present invention.

When it comes to using the present invention, the conducting body 33 having an ear contour in shape is plugged into the ear while the electrode 34 of the probe 32 is used to touch the inductive reflection zone 40 of vital points as shown in FIG. 1 and FIG. 2. With reference to FIG. 3, there are two blood vessels—the blood vessel 41 between the ear and the palm, as well as the blood vessel 42 between the ear and the bottom of the foot—in the human body forming respectively a conducting closed circuit. As the switch S1 is pressed to start the apparatus of the present invention, and the switch knob 26 is switched to "diagnosis", the oscillation current generated by the electronic oscillation generator will generate an electromagnetic wave through the magnet 35. According to the Chinese medical theory, there is an inductive reflection zone 40 (for instance, the vital point of ischium nerve 43 and the vital point 44 for indicating the presence of a cold as shown in FIG. 1) at the ear and at the hand corresponding to each respective organ, and any diseased organ will cause the corresponding inductive reflective zone to generate a positive reaction and the circulation magnetic field will also be changed. Consequently, when the electrode 34 of the probe 32 touches the diseased inductive reflection zone 40 of vital points, a sore feeling will be generated, and the switch knob 26 is then switched to "treatment" to perform treatment. One can press the push button 23, 23' to change the coefficient of resistance of the variable resistance R3 to further enhance or attenuate the current strength of oscillation so as to enhance or attenuate the electromagnetic wave, and the memory knob 24 and selection knob 25 can also be pressed (by another person to memorize a different strength of electromagnetic wave) and treat the inductive reflection zone 40 of the vital point. Moreover, since the present invention uses the conductive body 33 of the electrode unit 30 to plug into the ear while using the electrode 34 of the probe 32 to touch the inductive reflection zone 40 of the vital point at the palm or the bottom of the foot so as to perform two-way treatment similar to that of the acupuncture by use of the electromagnetic wave, the present invention possesses an enhanced effect. When a treatment process is set at about 5 minutes, counting as the first treatment process, a beep sound will be emitted from the speaker holes 27, and then the apparatus will enter into the second treatment process, which may also for example, be set at 5 minutes. In the event of a temporary stop, the starting knob 22 can be reset and the counter restarted to count back from 5 minutes, which can be shown in the first display zone, and the foregoing procedure can be referred to FIG. 8.

Although the present invention has been illustrated and described previously with reference to the preferred embodiment thereof, it should be appreciated that it is in no way limited to the details of such embodiment, but is capable of numerous modification within the scope of the appended claims.

What is claimed is:

1. A two-way medical treatment apparatus comprising:
   a housing containing a power supply and an electronic oscillation generator, said oscillation generator being connected to the power supply and arranged to generate an oscillating current; and
   an electrode unit having a first end arranged to be plugged into the housing to receive the oscillating current and a second end divided into a probe and a conducting body, the conducting body being shaped to fit within the ear of a patient and the probe being arranged to touch inductive reflecting zones of vital points in the palm or foot of the patient, as well as any possible curing points other than the vital points, and to form with the conducting body a closed circuit through a body of the patient, the probe including magnetic elements arranged to transform the oscillating current into an electromagnetic wave in order to stimulate the ear, palm, or bottom of the foot,
   wherein when said conductive body is situated in the ear of the patient and the probe is touched to an inductive reflective zone, the patient may feel soreness as the electromagnetic wave traverses a conductive passage in the patient, the presence or absence of pain being indicative of the presence of certain diseases, and
   wherein upon diagnosis of a particular disease or diseases, the probe may be touched to one of said vital points or curing points in order to simulate the effect of acupuncture needles and perform treatment of the particular disease or diseases.

2. A two-way medical treatment apparatus as claimed in claim 1, wherein the power supply includes a battery.

3. A two-way medical treatment apparatus as claimed in claim 1, wherein the power supply includes a transformer arranged to transform alternating current into direct current to be supplied to the electronic oscillation generator.

4. A two-way medical treatment apparatus as claimed in claim 1, wherein said conducting body is made of a gel shaped to fit within the ear.

5. A two-way medical treatment apparatus as claimed in claim 1, wherein said housing further includes an LED digital display board, said LED digital display board including a first display area for displaying an elapsed time of a diagnosis or treatment procedure, a second display area for displaying a magnitude of the electromagnetic wave, and a third display area for displaying a battery charge.

6. A two-way medical treatment apparatus as claimed in claim 1, wherein said electronic oscillation generator includes a variable resistance for controlling a current strength of the oscillating current, thereby controlling an amplitude of the electromagnetic wave.

* * * * *